United States Patent [19]

Richards et al.

[11] 3,996,626
[45] Dec. 14, 1976

[54] ARTIFICIAL INTRAOCULAR LENS

[75] Inventors: William Richards, Medway; Bernard Grolman, Worcester, both of Mass.

[73] Assignee: American Optical Corporation, Southbridge, Mass.

[22] Filed: Sept. 22, 1975

[21] Appl. No.: 615,275

Related U.S. Application Data

[63] Continuation-in-part of Ser. No. 606,032, Aug. 20, 1975, abandoned.

[52] U.S. Cl. .................................... 3/13; 29/520
[51] Int. Cl.² ......................................... A61F 1/24
[58] Field of Search ............... 3/13, 1; 351/160

[56] References Cited

UNITED STATES PATENTS

| | | | |
|---|---|---|---|
| 3,673,616 | 7/1972 | Fedorov et al. | 3/13 |
| 3,906,551 | 9/1975 | Otter | 3/13 |

*Primary Examiner*—Ronald L. Frinks
*Attorney, Agent, or Firm*—H. R. Berkenstock, Jr.; William C. Nealon

[57] ABSTRACT

A lens suitable for implantation in the eye is provided with laterally extending iris clips each having at least one of its ends locked within the body of the lens. The clips are initially extended through close-fitting openings, terminally beaded and forcefully retracted sufficiently to bury their beaded ends within the lens body. Cold flow of lens material around the beaded ends locks the clips in place.

12 Claims, 20 Drawing Figures

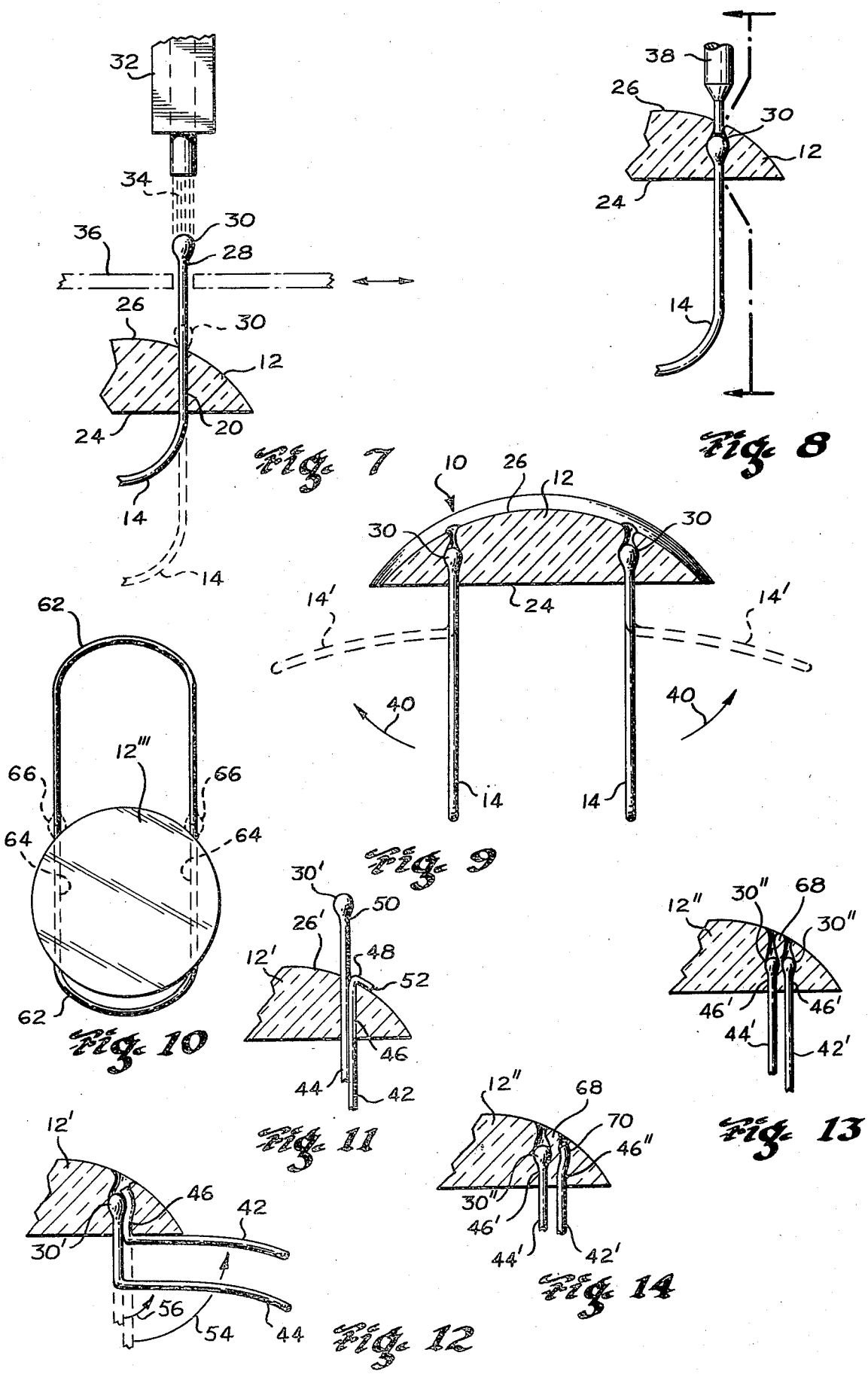

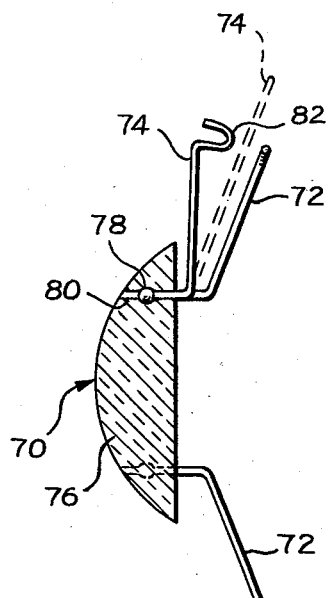
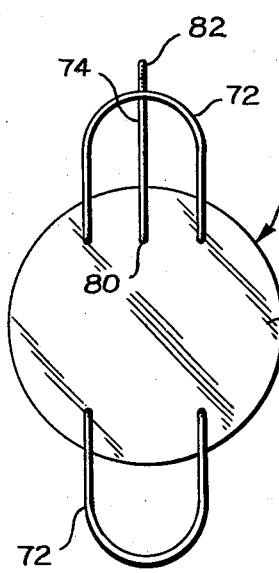
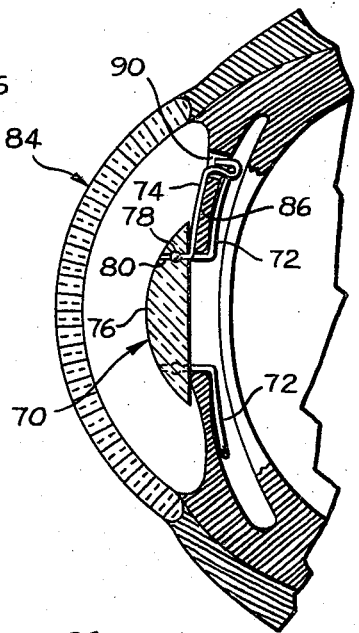
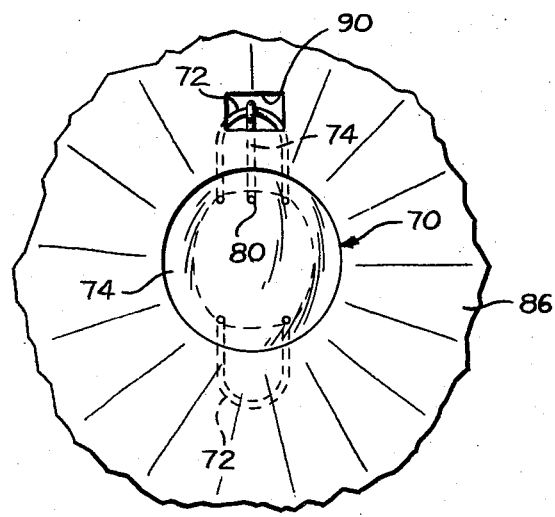
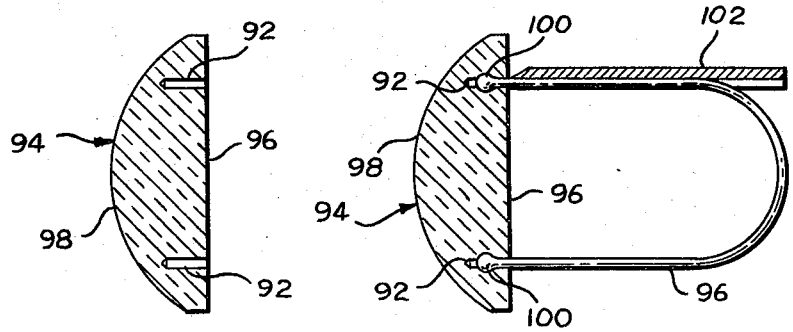

ARTIFICIAL INTRAOCULAR LENS

This is a continuation-in-part of application Ser. No. 606,032 filed Aug. 20, 1975, now abandoned.

BACKGROUND OF THE INVENTION

1. Field of the Invention

This invention relates to improvements in ophthalmology and more particularly to improvements in artificial intraocular lenses (pseudophakoi) used for the correction of aphakia and re-establishment of binocularity in aphakia.

2. Discussion of the Prior Art

Well-fixed and well-centered intraocuar lens implants are known to produce stable retinal images with stable space localization and offer the best chance of re-establishment of binocularity in cases of aphakia.

Many techniques of lens implantation, including suturing to the ciliary muscle as disclosed in U.S. Pat. No. 3,711,870 and iris diaphragm fixation as disclosed in U.S. Pat. No. 3,673,616 for example, have been used. The latter is considered to be a safe procedure giving good stability and the present invention deals with improvements in this general type of pseudophakos. More particularly, the invention relates to improvements in "iridocapsular" and/or "iris clip" implants having a fastening section comprised of posterior and/or anterior iris clips which may be in the form of loops or struts of wire or wire-like material.

Heretofore, iris clips have been fastened by extending ends thereof into holes drilled or otherwise formed in the lenses. Anchoring against accidental withdrawal and disconnection from the lens has, however, presented the serious problem of having to establish and maintain exacting tolerances of hole and wire size for fitting and/or the use and dependence upon cements.

The latter, in requiring adhesive materials which are biologically inert and resistant to absorption or deterioration by human body fluids, not to mention having to be strong bonding, leaves few materials to choose from and less than optimum product dependability. There is an attending possibility of subsequent deterioration of the bonded materials, if not the cement, causing loosening or detachment of parts in the eye.

Press fitting, on the other hand, which eliminates the additional material of cements but requires exacting tolerances of hole and wire size as already mentioned, presents exceptional manufacturing problems. The miniaturization of lenses and the wire size of clips and anchoring hole diameters required of pseudophakoi are alone problematic, not to mention compounding thereof by requirements for press fit tolerances. Tediousness and high scrap yield seriously limit production output and contribute to high, if not excessive, product cost, all without assurance that material erosion or decomposition will not occur to the extent of loosening ro disconnection of parts under prolonged usage.

Additionally, all pseudophakoi require sufficient sturdiness of structure to withstand relatively harsh manipulation and adjustment of parts by the surgeon prior to and/or during implantation. Thus, an assurance against accidental disconnection of parts is urgently sought.

It is, accordingly, a principal object of the present invention to provide an improved pseudophakos and method of making same wherewith positive locking together of lens and iris clips may be accomplished relatively simply, quickly and economically to maximize manufacturing output, minimize product cost and provide both the surgeon and recipient with an assurance against disconnection of its parts.

SUMMARY OF THE INVENTION

The aforesaid object and its corollaries are accomplished by locking ends of the iris clips of pseudophakoi within the material of the lens body. Openings are provided in the lenses completely through and beyond which ends of the clips are initially extended. They are then beaded mechanically or with the application of heat and forcefully retracted sufficiently to bury their beaded ends within the lens body. Cold flow of the lens material around the enlarged beaded ends locks the clips in place.

Details of the invention will become more readily apparent from the following description when taken in conjunction with the accompanying drawings.

IN THE DRAWINGS

FIGS. 6, 7, 8 and 9 are illustrations of the method of applying iris clips to the pseudophakos of FIGS. 1 and 2 according to the invention;

FIG. 10 illustrates a technique for applying anterior iris clips to the pseudophakos of FIG. 4;

FIGS. 11 and 12 are illustrations of a techinque contemplated for applying iris clips of types shown in FIGS. 3 and 5 to pseudophakoi;

FIGS. 13 and 14 are illustrations of other modifications of the invention;

FIG. 15 is a vertical cross-sectional view of still another modification of the invention;

FIG. 16 is a rear elevational view of the pseudophakos shown in FIG. 15;

FIG. 17 is an illustration in cross-section of an intraocular implantation of the pseudophakos of FIGS. 15 and 16;

FIG. 18 is a fragmentary front elevational view of the implanted pseudophakos;

FIG. 19 is a cross-sectional view of a partially completed pseudophakos wherewith another modification of the invention is illustrated; and FIG. 20 is a view in cross-section of the pseudophakos of FIG. 19 showing steps taken toward its completion.

DESCRIPTION OF THE PREFERRED EMBODIMENTS

Figure 1:
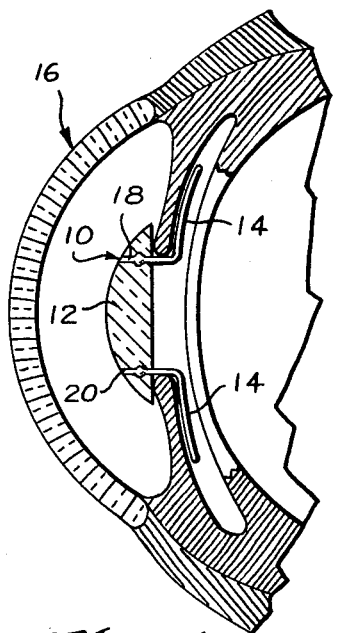
FIG. 1 is an illustration, in cross-section, of a preferred embodiment of a pseudophakos insitu.
Figure 2:
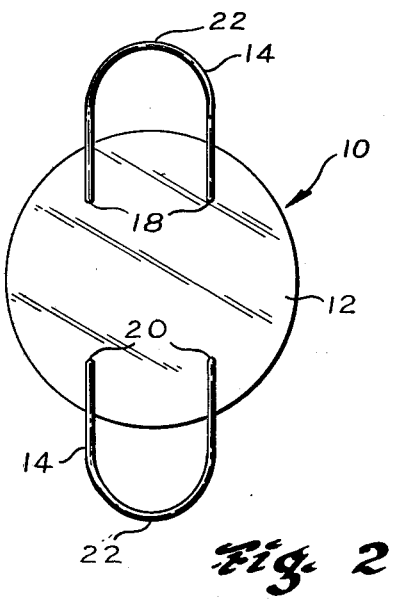
FIG. 2 is a rear elevational view of the pseudophakos of FIG. 1.

Referring more particularly to FIGS. 1 and 2 of the drawings, pseudophakos 10 comprises a lens 12 having a pair of posterior iris clips 14 for fixturing within eye 16. This form of pseudophakos is commonly referred to as an "iridocapsular lens" or "two-loop lens". Its fixation is in the iridocapsular cleft substantially as illustrated in FIG. 1.

Lens 12 is formed of a material which is biologically inert, i.e. not susceptible to being absorbed by body fluids and capable of being well tolerated by the human body when implanted. Exemplary materials are methylmethacrylate resins such as those available under the tradenames "Lucite" and "Plexiglass" and biologically neutral chemically pure polymethylmethacrylates or biologically inert polymeric materials.

Iris clips 14 which comprise loops of wire having their opposite ends secured to lens 10 are, for reasons of avoiding irritation and/or human body rejection, formed of a biologically inert material such as platinum, titanium, tantalum or an extruded polyamide such as nylon or one or more of the other aforementioned plastic materials.

Iris clips 14 and others to be described hereinafter will be referred to as being "wire" or "formed of wire". Accordingly, it should be understood that the term "wire" as used in this specification and its appended claims is intended to include strands, strips, rods or fibers of biologically inert material whether the material is metallic or plastic and whether one or both is used to make up a particular array of iris clips.

A technique for securing clips 14 to lens 12 according to the invention is illustrated in FIGS. 6–9 and involves the following procedure:

Lens 12 is provided with pairs of openings 18 and 20 (FIGS. 1 and 2). These openings and the wire size of iris clips 14 are controlled to be of such relative diametral dimensions as to permit passage of opposite ends of clips 14 through openings 18 and 20 preferably only with sufficient clearance for a forceful sliding fit.

Figure 6:
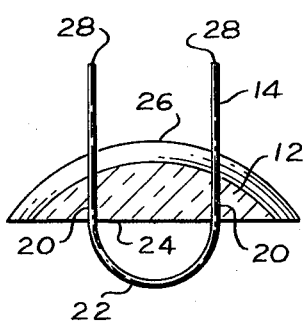

Each of clips 14, having been provided with a bight 22 which produces the illustrated U-shape, is inserted into a pair of openings, e.g. openings 20 (FIG. 6), and forced completely through such openings in a direction from the posterior side 24 to the anterior side 26 of lens 12. Each loop 14 is preferably extended through openings 20, or 18, to the maximum extent permitted by bight 22 as illustrated in FIG. 6, for example. In so doing, termini 28 of clips 14 are brought to positions clear of the anterior surface 26 of lens 12 as illustrated in FIG. 6. Thus, the working of termini 28 mechanically or with the application of heat to form beads 30 thereon (FIGS. 7–9) can be accomplished without harm to lens 12.

Having so extended iris clip 14 through lens 12, e.g. as shown in FIG. 6, its termini 28 are each provided with an enlarged head or bead 30 as illustrated in FIGS. 7–9. This may be accomplished by heating each terminus 28 sufficiently to induce beading by surface tension forces. Laser 32 has been depicted diagrammatically in FIG. 7 as directing a high intensity beam 34 against terminus 28 for this purpose. Terminus 28 is melted sufficiently to permit beading to take place, i.e. as a result of surface tension forces resisting the flow of molten material.

It has been determined that a pulsed neodymium laser having its emission (beam 34) carefully coaxially aligned with terminus 28 of clip 14 will not damage lens 12 under conditions depicted in FIG. 7, for example. However, a heat shield 36 may be moved into place between terminus 28 and lens 12 as an assurance against lens damage by misalignment of the laser or in cases where other heat sources such as flame or radiant energy may be used to effect beading.

Having so formed a bead 30 upon each end of iris clip 14, the clip is retracted to the point where beads 30 resist entering openings 20, e.g. as shown by dot-dash outline in FIG. 7. From this point, clips 14 are forcefully further pulled and/or driven into the material of lens 12. A punch 38 (FIG. 8) directed against beads 30 may be used. By so forcing the enlarged heads or beads 30 of termini 28 into lens 12, a cold flow of material of the lens around beads 30 permanently locks clips 14 thereinplace as illustrated in FIGS. 8 and 9.

Completion of the pseudophakos requires only a shaping of the retracted clips 14 by bending each laterally in the directions of arrows 40 to substantially the positions shown by dot-dash outline 14' (FIG. 9).

It is to be understood that the retraction of beaded ends of clips 14 into the material of lens 12 as explained in connection with FIGS. 7 and 8 may be facilitated by ultrasonically vibrating punch 38 and/or the material of clips 14. It is the intention of the invention to bury the beads 30 of the termini 28 within the lens body by whatever technique is deemed most appropriate and thereby cause a cold flow of lens material around beads 30 to permanently lock the clips 14 in place.

Figure 3:
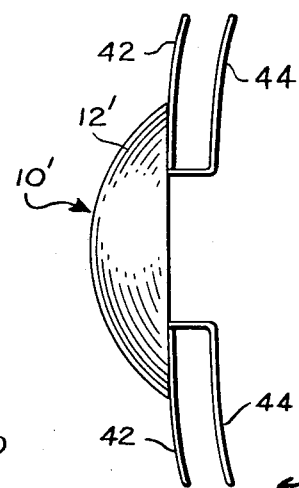
FIG. 3 is a side view of a modification of the invention.

Exemplary and useful but not necessarily restrictive wire sizes (diameters) for clips 14 and others to be referred to herein are from 0.1 to 0.2 mm with beads 30 representing an increase in diameter of approximately from 10 to 20 percent.

in FIG. 3 there is illustrated a modification of the invention wherein pseudophakos 10' is provided with both anterior and posterior iris clips 42 and 44 which, for purposes of this illustration, will be considered as each comprising a loop of wire similar to the configuration of any one or clips 14 described hereinabove. Such a pseudophakos is commonly referred to as an "iris-clip lens" or "four-loop lens". It may be used after extracapsular extraction but is more commonly used after intracapsular surgery. In use, fixation is on the iris diaphragm with the diaphragm disposed between clips 42 and 44.

Fixation of clips 42 and 44 in lens 12' is accomplished in the manner illustrated in FIGS. 11 and 12. Clips 42 and 44, prior to lateral bending thereof into the configurations of FIG. 3, are placed with their corresponding ends in juxtaposition and inserted together through openings 46 (FIG. 11). Openings 46 are each sized to accomodate, with a snug but sliding fit, the dual wires of a corresponding pair of iris clip ends. Ends 48 and 50 of clips 42 and 44 respectively in FIG. 11 represent one such pair.

After insertion, end 50 of posterior clip 44 is extended a substantial distance beyond the anterior surface 26' of lens 12' and provided with bead 30' in the manner described relative to the formation of bead 30 in FIGS. 7 and 8. End 48 of anterior clip 42 is bent over and against surface 26' to form hook 52 which prevents its retraction in lens 12'. Posterior clip 44 is then forcefully retracted, e.g. pushed with punch 38 of FIG. 8 and/or ultrasonically urged into the material of lens 12' as shown in FIG. 12. Cold flow of both the material of lens 12' and that of the adjacent end of anterior clip 42 effect a simultaneous locking of both clips 44 and 42 in lens 12'.

Finally, clips 44 and 42 are bent laterally in the direction of arrows 54 and 56 respectively to assume a desired orientation and shape for subsequent intraocular implantation. Hook 52 of iris clip 42 may be removed, e.g. ground or snipped away.

Figure 5:
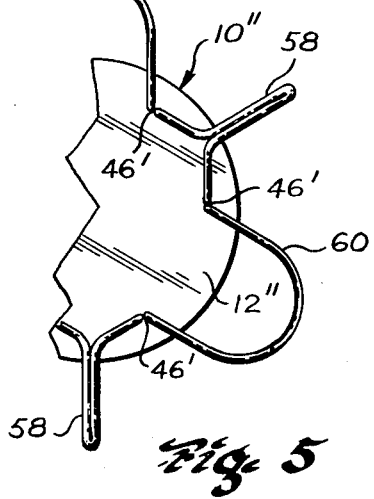

The securing together of a pair of corresponding ends of both anterior and posterior iris clips in the manner illustrated in FIGS. 11 and 12 is applicable to other forms of pseudophakoi. For example, a pseudophakos 10", shown in fragmentary rear elevation (FIG. 5)

having anterior struts 58 and posterior loops 60 is exemplary of such an alternative structure. Openings 46' extending completely through lens 12" may each simultaneously receive one end of one loop 60 and an end of an adjacent strut 58. In each case, either the end of loop 60 or the end of strut 58 will be beaded and forced into the material of lens 12" to produce the locking effect shown and described in connection with FIGS. 11 and 12. The finishing of pseudophakos 10" would include steps of bending struts 58 immediately adjacent the anterior surface of lens 12" in such manner as to cause them to extend laterally against the lens. Loops 60 are then provided with bends directing them laterally but spaced away from the posterior surface of lens 12" to provide a channel space between struts 58 and clips 60 for receiving the iris diaphragm of an aphakic eye.

Figure 4:
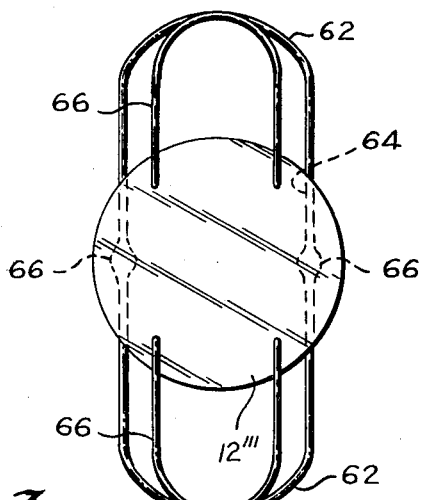
FIGS. 4 and 5 are rear elevational views of further modifications of the invention.

A still further modification of the invention is shown in FIG. 4 wherein it is contemplated that anterior iris clips 62 be anchored in chordal openings 64 extending through an implantable lens 12'''. Posterior clips 66 being substantially identical to clips 14 of pseudophakos 10 in FIGS. 1 and 2 would, accordingly, be anchored in lens 12''' in the manner illustrated relative to clips 14 in FIGS. 6-8.

Referring more particularly to the technique contemplated for anchoring anterior clips 62, reference is made to FIG. 10. Therein it can be seen that one of clips 62 is inserted completely through lens 12''' in parallel chordal openings 64. The other of clips 62 is butted end-for-end with the inserted clip and the two are welded, brazed, soldered or fused together. Enlargements, i.e. beads 66, may be produced by displacement of molten materials of the abutted ends of clips 62 or an addition of soldering, welding or brazing material.

Retraction of clips 62 in lens 12''' to the extent of pulling beads 66 thereinto as shown in FIG. 4 effects the locking of clips 62 in place by causing a cold flow of lens material around the beads. Ultrasonic vibration of clips 62 during the aforesaid retraction can facilitate the operation and enhance the necessary cold flow of lens material.

Other modifications of the invention are illustrated in FIGS. 13 and 14 wherein dual parallel openings 46' are provided in lens 12" for the reception of ends of anterior and posterior iris clips 42' and 44' which are of similar configuration (i.e. loops) to clips 42 and 44 respectively of the FIGS 11 and 12 embodiment of the invention. One of clips 42' and 44' may alternatively be shaped into the configuration of a strut, if desired.

In the case of the embodiment of the invention illustrated in FIG. 13, however, each of clips 42' and 44' and its terminus provided with a bead 30" which is forced into lens 12" and embedded therein by displacement of material of the lens including thin wall 68. This material displacement effects permanent locking of the clips within lens 30".

As illustrated in FIG. 14, clips 42' and 44' may similarly locked in place with the provision of one bead 30" only.

For example, with bead 30" on clip 44' and both clips forced into the material of lens 12", bead 30" in this instance will produce a lateral displacement, i.e. bulging, of wall 68 and end 70 of clip 46'. This, together with other lens material flow partially over bead 30" and end 70 effects the iris clip permanent locking feature of the invention.

Still another modification of the invention is illustrated in FIGS. 15 and 16. This relates to a pseudophakos 70 having a pair of posterior iris clips 72 and an anterior fastening wire which will be referred to hereinafter as clasp 74.

Clips 32 are anchored within the body of lens 76 in the manner described in connection with the FIGS. 1 and 2 embodiment of the invention, i.e. they are preferably each formed into the configuration of a loop having its opposite ends enlarged and forced into the lens material.

Clasp 74, comprising a length of wire, is similarly anchored in the material of lens 76. Its proximal end is provided with bead 78 which is forced into opening 80 of smaller diametral dimension. Displacement of lens material around bead 78 locks the clasp in place.

Clasp 74, preferably being formed of the same type of material as that of clips 72, is annealed and/or selected from stock which is highly malleable. Clips 72, while bendable, are not readily deformable and resist deforamtion of shapes initially imparted thereto. The use of identical metallic materials will avoid chances of the pseudophakos creating an electromotive force intraocular fluids. However, clasp 74 and/or clips 72 may alternatively be formed of biologically inert plastic materials which are non-electrically conductive but have workable characteristics similar to those desired of the aforesaid metal counterparts.

Clasp 74 may have its distal end 82 preformed to the configuration of an open hook as shown with full line illustration in FIGS. 15 and 16 or extended substantially straight-out as depicted with broken lines 74' in FIG. 15 thereby lending itself to subsequent reshaping.

Pseudophakos 70 is intended to be intraocularly implanted with its clips 72 located posteriorly of the iris. Eye 84 having iris 86 has been illustrated in FIGS. 17 and 18.

Fastening of the pseudophakos for greater assurance against luxation is then accomplished by directing the terminal portion, i.e. the end 82 of clasp 74, through an iridectomy 90 (FIGS. 17 and 18) and around clip 72.

All illustrations of techniques for embedding ends of lens components (clips or clasps) have thus far related to the provision and use of holes in lenses which extend completely therethrough, i.e. holes that have open opposite ends. However, for greater assurance against roughening of anterior surfaces of the lenses, e.g. by drilling therethrough and/or removing hole-edge burrs or other material displacements, blind holes such as holes 92 in lens 94 of FIG. 19 may be used. Holes 92 extend from the posterior side 96 of lens 94 toward its anterior side 98 but do not break through side 98.

An iris clip 96 to be anchored in lens 98 would, for example, have a wire diameter approximately equal to that selected for holes 92, or vice versa, be provided with terminal enlargements or beads 100 and forced into openings 92. A semi-circularly channeled punch 102 (FIG. 20) or any other suitable tool or tools may be used to facilitate the insertion of beads 100. Initial displacement and return cold flow of lens material around the necks of beads 100 will produce the desired locking of clip 96 in place.

It is to be understood that all operations of forcing terminal enlargements (beads 30, 30', 30", 78, 100) or other parts of iris clips into materials of lenses receiving same may be facilitated by warming the lens material in each case with concentrated visible light, e.g. light produced by a tungsten filament lamp placed close to the lens material or focused thereupon. Other sources of heat may be employed. Use of the expression "cold flow" herein is intended to refer to the viscous flow of material caused by forces applied thereto at ordinary temperatures, i.e. without melting of the material. Warming of the lens material as described herein is not to be interpreted as exceeding said ordinary temperatures.

The embodiments of the invention described hereinabove for purposes of illustration are not to be interpreted as restrictive of the invention beyond that necessitated by the following claims. Those skilled in the art will readily appreciate that there are other modifications and adaptations of precise forms here shown which may be made to suit particular requirements.

We claim:

1. A pseudophakos comprising:
  a lens of material suitable for implantation in the eye and having a number of openings of a predetermined diametral size extending thereinto;
  an iris clip formed of a length of wire, at least one end of which is extended into one of said openings, said end of said length of wire terminating with an enlargement of substantially greater cross-sectional size than the diametral size of said opening and being embedded in a surround of the material of said lens, said surround locking said iris clip in place.

2. A pseudophakos according to claim 1 including a plurality of iris clips each formed of a length of wire and having their corresponding opposite ends terminally enlarged and embedded in said material of said lens.

3. A pseudophakos according to claim 2 wherein said plurality of iris clips include both anterior and posterior configurations respectively spaced apart for reception of an intraocular iris diaphragm therebetween.

4. A pseudophakos according to claim 2 wherein said iris clips are each in the configuration of a loop.

5. A pseudophakos according to claim 2 wherein some of said plurality of iris clips are in the form of a loop and others are in the configuration of a strut.

6. A pseudophakos according to claim 2 wherein one end of each of a pair of said iris clips are placed in juxtaposition within one of said openings in said lens and embedded in said surround of said material of said lens.

7. A pseudophakos according to claim 6 wherein the terminus of only one of said pair of juxtapositioned ends of said iris clips is provided with an enlargement.

8. A pseudophakos according to claim 2 wherein said plurality of iris clips includes a pair of loops of wire having their corresponding ends substantially axially aligned, butted and secured together with an enlargement of intregal material, said enlargements being embedded in said surround of the material of said lens for locking said pair of loops in place.

9. A pseudophakos according to claim 1 including a clasp formed of a length of malleable wire, said clasp having a proximal enlargement disposed within another of said openings and locked thereinplace by a surround of the material of said lens.

10. A pseudophakos according to claim 9 wherein said clasp is formed of the same type of material as said iris clip but rendered relatively highly malleable.

11. A pseudophakos according to claim 1 wherein said openings extend only partially through said lens.

12. A pseudophakos according to claim 11 wherein said lens has a convex anterior surface and said openings extend from an opposite posterior side thereof toward said anterior surface.

* * * * *